United States Patent [19]

Baumgarth et al.

[11] Patent Number: 5,495,022

[45] Date of Patent: Feb. 27, 1996

[54] PIPERIDINES AND PIPERAZINES

[75] Inventors: Manfred Baumgarth; Inge Lues, both of Darmstadt; Klaus-Otto Minck, Ober-Ramstadt; Norbert Beier, Reinheim, all of Germany

[73] Assignee: Merck Patent Gesellschaft Mit Beschrankter Haftung, Darmstadt, Germany

[21] Appl. No.: 264,872

[22] Filed: Jun. 24, 1994

[30] Foreign Application Priority Data

Jun. 26, 1993 [DE] Germany ............... 43 21 366.9

[51] Int. Cl.$^6$ ............... C07D 211/22; C07D 405/06; C07D 401/06; A61K 31/455; A61K 31/495

[52] U.S. Cl. ............... 546/165; 546/196; 546/195; 544/375; 544/392

[58] Field of Search ............... 546/165, 195, 546/196; 514/314, 317, 320, 255; 544/375, 392

[56] References Cited

U.S. PATENT DOCUMENTS

| | | | |
|---|---|---|---|
| 4,302,589 | 11/1981 | Fanshawe et al. | 546/201 |
| 4,977,166 | 12/1990 | Hardy et al. | 514/323 |
| 5,194,437 | 3/1993 | Peglion et al. | 514/495 |

FOREIGN PATENT DOCUMENTS

| | | |
|---|---|---|
| 300908 | 7/1988 | European Pat. Off. . |
| 490772 | 12/1991 | European Pat. Off. . |

OTHER PUBLICATIONS

Beregi et al., J. of Pharm. & Exper. Ther., vol. 263, No. 3, pp. 1369–1376. (1992).
Millan et al., J. of Pharm. & Exper. Ther., vol. 268, No. 1, pp. 337–352 (1994).
Misztal et al., Pol. J. Pharmacool. Pharm., vol. 36, pp. 697–703, (1964).

Primary Examiner—David B. Springer
Attorney, Agent, or Firm—Millen, White, Zelano & Branigan

[57] ABSTRACT

Piperidine and piperazine derivatives of formula I

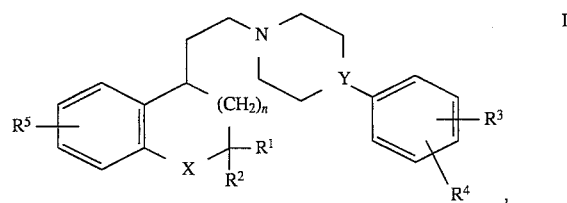

wherein
$R^1$ and $R^2$ are H or A,
$R^3$, $R^4$ and $R^5$ are each independently H, Hal, OH, OA, OAc, $NO_2$, $NH_2$, NHAc, $NHSO_2A$ or CN, or
$R^3$ and $R^4$ together are $—O—(CH_2)_m—O—$,
n is 0, 1 or 2
X is O or $CH_2$, if n=0 or 2, or $CH_2$, NH, NA or NAc, if n=1,
Y is CH or N,
m is 1 or 2,
Hal is F, Cl, Br or I,
A is $C_{1-6}$-alkyl,
Ac is $C_{1-8}$-alkanoyl $C_{1-10}$-aralkanoyl or $C_{7-11}$-aroyl,
and their physiologically acceptable salts show antiarrhythmic effects.

15 Claims, No Drawings

PIPERIDINES AND PIPERAZINES

SUMMARY OF THE INVENTION

The invention relates to novel piperidine and piperazine derivatives of the formula I

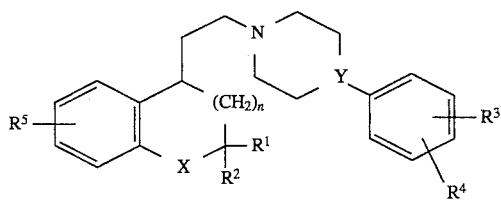

in which
$R^1$ and $R^2$ are H or A,
$R^3$, $R^4$ and $R^5$ in each case independently of one another are H, Hal, OH, OA, OAc, $NO_2$, $NH_2$, NHAc, $NHSO_2A$ or CN, or
$R^3$ and $R^4$ together are also $—O—(CH_2)_m—O—$
n is 0, 1 or 2
X is O or $CH_2$, if n=0 or 2, or $CH_2$, NH, NA or NAc, if n=1,
Y is CH or N
m is 1 or 2
Hal is F, Cl, Br or I,
A is alkyl having 1–6 C atoms and
Ac is alkanoyl having 1–8 C atoms, aralkanoyl having 1–10 C atoms or aroyl having 7–11 C atoms,
and their physiologically acceptable salts.

An object of the invention was to find novel compounds which can be used for the preparation of medicaments.

It was found that the compounds of the formula I and their physiologically acceptable acid addition salts have useful pharmacological properties and good tolerability. Thus, they show, in particular, antiarrhythmic effects and positive inotropic effects which prolong the refractory period of the heart.

The effect on the heart can be determined e.g. on anaesthetized or conscious rats, guinea-pigs, dogs, cats, apes or mini-pigs and the positively inotropic effect can also be determined in isolated heart preparations (e.g. auricle, papillary muscle or perfused whole heart) of the rat, guinea-pig, cat or dog, e.g. by methods such as described in Arzneimittelforschung, Volume 31 (I) No. 1a (1981), pages 141 to 170, or by Schliep et al. in the 9th International Congress of Pharmacol., London (1984), Abstracts of papers 9P.

The compounds can therefore be used as pharmaceutical active substances in human and veterinary medicine. They can further be used as intermediates for the preparation of other pharmaceutical active substances.

The invention accordingly relates to the compounds of the formula I, their acid addition salts and to a process for their preparation, characterized in that a compound of the formula II

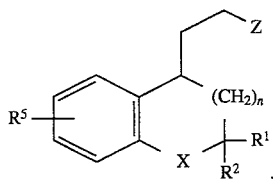

in which
Z is Cl, Br, OH or a reactive, functionally modified OH group and
$R^1$, $R^2$, $R^5$, X and n have the meanings indicated, is reacted with a compound of the formula III

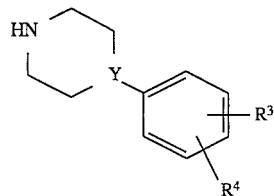

in which
$R^3$, $R^4$ and Y have the meanings indicated, or in that a compound which corresponds per se to the formula I, but instead of one or more $CH_2$ groups has one or more reducible groups, is converted into a compound of the formula I by reduction with a suitable reducing agent and/or in that one or more of the radicals $R^3$, $R^4$ and/or $R^5$ or X respectively in a compound of the formula I are converted into other radicals $R^3$, $R^4$ and/or $R^5$ or X respectively and/or in that a basic compound of the formula I is converted into one of its physiologically acceptable acid addition salts by treating with an acid.

Hereinbefore and hereinafter, $R^1$, $R^2$, $R^3$, $R^4$, $R^5$, n, m, X, Y, Z, Hal, A and Ac have the meanings indicated in the formulae I, II and III, if not expressly stated otherwise.

The radical A is alkyl having 1, 2, 3, 4, 5 or 6, in particular 1, 2 or 3, C atoms, preferably methyl, and further also ethyl, n-propyl, isopropyl, n-butyl, isobutyl, sec-butyl or tert-butyl. OA is preferably methoxy, and further also ethoxy, n-propoxy, isopropoxy, n-butoxy, isobutoxy, sec-butoxy or tert-butoxy. In —NA— or $NHSO_2A$, A is preferably methyl.

The group Ac is preferably alkanoyl having 1–8 C atoms, in particular having 1, 2, 3, 4 or 5 C atoms; in specifically preferably acetyl, and further preferably formyl, propionyl, butyryl, isobutyryl, valeryl, isovaleryl or pivaloyl (trimethylacetyl), additionally preferably optionally substituted aroyl having 7–15 C atoms, suitable substituents in particular being 1–3, preferably one, of the following groups: alkyl, alkoxy, alkylthio, alkylsulfinyl or alkylsulfonyl in each case having 1–3, preferably 1 or 2, C atoms, methylenedioxy, and further OH, F, Cl, Br, I, $NO_2$, $NH_2$, alkylamino or dialkylamino in each case having 1–3, preferably 1 or 2, C atoms in the alkyl group. Individual preferred aroyl radicals are benzoyl, o-, m- or p-toluyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylthiobenzoyl, o-, m- or p-methylsulfinylbenzoyl, o-, m- or p-methylsulfonylbenzoyl, 2,3- or 3,4-methylenedioxybenzoyl or 1- or 2-naphthoyl. Ac can furthermore be aralkanoyl having 1–10 C atoms such as e.g. phenylacetyl, 2- or 3-phenylpropionyl or 2-, 3- or 4-phenylbutyryl.

If a compound of the formula I, II or III contains two or more groups A and/or Ac, these can be identical to or different from one another.

The radicals $R^1$ and $R^2$ are preferably in each case hydrogen or methyl.

$R^3$, $R^4$ and $R^5$ are in each case preferably hydrogen or methoxy; $R^5$ is also CN, while $R^3$ and $R^4$ together can also preferably be methylenedioxy or ethylenedioxy.

The meaning of X is oxygen or $—CH_2—$, if n is 0 or 2. If n=1, however, X is $—CH_2—$, $—NH—$, $—NA—$ or $—NAc—$, where A and Ac have the abovementioned meanings. Y is N, but preferably CH.

The invention accordingly relates in particular to those compounds of the formula I in which at least one of the radicals mentioned has one of the abovementioned meanings, in particular the abovementioned preferred meanings.

Some preferred groups of compounds can be expressed by the following sub-formulae Ia to Ii, which correspond to the formula I and in which the radicals and parameters not described in greater detail have the meaning indicated in the formula I, but in which in Ia $R^1$, $R^2$ and $R^5$ are hydrogen and $R^3$ and $R^4$ are in each case methoxy;
in Ib $R^1$, $R^2$ and $R^5$ are hydrogen and $R^3$ and $R^4$ together are methylene- or ethylenedioxy;
in Ic $R^1$, $R^2$ and $R^5$ are hydrogen, n is 0, 1 or 2 and X is —$CH_2$—;
in Id $R^1$, $R^2$ and $R^5$ are hydrogen, n is 0 or 2 and X is oxygen;
in Ie $R^1$, $R^2$ and $R^5$ are hydrogen, n=1 and X is NH;
in If $R^1$, $R^2$ and $R^5$ are in each case hydrogen, $R^3$ and $R^4$ are methoxy, X is —$CH_2$— and Y is CH;
in Ig $R^1$, $R^2$ and $R^5$ are hydrogen, $R^3$ and $R^4$ are in each case methoxy, X is —$CH_2$— and Y is nitrogen;
in Ih $R^1$, $R^2$ and $R^5$ are hydrogen, $R^3$ and $R^4$ together are ethylenedioxy, X is —$CH_2$— and Y is nitrogen;
in Ii $R^1$ and $R^2$ are in each case methyl, $R^5$ is hydrogen and $R^3$ and $R^4$ are in each case methoxy:

The compounds of the formula I are otherwise prepared by methods known per se, as are described in the literature (e.g. in the standard works such as Houben-Weyl, Methoden der Organischen Chemie [Methods of Organic Chemistry], Georg-Thieme-Verlag, Stuttgart), namely under reaction conditions which are known and suitable for the reactions mentioned. Use can also be made here of variants which are known per se but not mentioned in greater detail here.

If desired, the starting substances for the claimed process can also be formed in situ such that they are not isolated from the reaction mixture, but immediately reacted further to give the compounds of the formula I.

The starting substances of the formula II and III are known in some cases. If they are not known, they can be prepared by methods known per se. Compounds of the formula II are prepared, for example, starting from indan-1-one, 6,7,8,9-tetrahydro-5H-benzocyclohepten-5-one, 1,2,3,4-tetrahydronaphthalen-1-one, 2,3-dihydrobenzofuran-3-one, 2,3,4,5-tetrahydro-1-benzoxepin-5-one or 1,2,3,4-tetrahydro-quinolin-4-one or their substituted derivatives respectively, by reaction with diethylethoxycarbonyl-methane phosphonate (Wittig-Horner Reaction; Org. Reactions 25, 73 (1977)), then reduction with $H_2$/Pd-C, reduction of the resulting product with diborane and if desired further activation of the radical Z by conversion into another radical Z according to methods known per se but not mentioned in greater detail here.

The compounds of the formula III can be obtained, for example, by reaction of di(2-chloroethyl)amine with aniline or with an appropriate derivative of aniline substituted on the phenyl ring. The piperidines of the formula III are accessible e.g. by reaction of $NH_3$ with 1,5-dichloro-3-phenylpentane or with compounds substituted homologously on the phenyl ring.

The reaction of the compounds II and III proceeds according to methods such as are known from the literature for the alkylation of amines. The components can be fused with one another without the presence of a solvent, if desired in a closed tube or in an autoclave. However, it is also possible to react the compounds in the presence of an indifferent solvent. Suitable solvents are e.g. hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, and if desired also mixtures of these solvents with one another or mixtures with water. The addition of an acid-binding agent, for example of an alkali metal hydroxide, carbonate or bicarbonate or alkaline earth metal hydroxide, carbonate or bicarbonate or another salt of a weak acid of the alkali metals or alkaline earth metals, preferably of potassium, sodium or calcium, or the addition of an organic base such as triethylamine, dimethylaniline, pyridine or quinoline or of an excess of the amine component can be favourable. Depending on the conditions used, the reaction time is between a few minutes and 14 days and the reaction temperature is between about 0° and 150°, normally between 20° and 130°.

It is further possible to obtain a compound of the formula I by reducing a compound which corresponds per se to the formula I, but instead of one or more $CH_2$ groups contains one or more reducible groups, preferably at temperatures between −80° and +250° in the presence of at least one inert solvent.

Reducible groups (replaceable by hydrogen) are in particular oxygen in a carbonyl group, hydroxyl, arylsulfonyloxy (e.g. p-toluenesulfonyloxy), N-benzenesulfonyl, N-benzyl or O-benzyl.

It is in principle possible to convert compounds which contain only one group, or those which contain two or more of the abovementioned groups next to one another, reductively to a compound of the formula I. Preferably, nascent hydrogen or complex metal hydrides are used for this, further Wolff-Kishner reduction and also reductions using hydrogen gas with transition metal catalysis.

Preferred starting substances for the reduction correspond to the formula IV

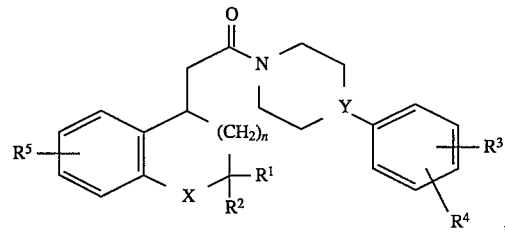

in which
$R^1$, $R^2$, $R^3$, $R^4$, $R^5$, X and Y have the meanings previously indicated for the formula I.

Compounds of the formula IV can be prepared by reaction of compounds which correspond per se to the formula II, but instead of the —$CH_2$—Z group contain a —COCl or —COBr group, with piperidines or piperazines of the formula III.

If nascent hydrogen is used as the reducing agent, this can be generated e.g. by treatment of metals with weak acids or with bases. Thus e.g. a mixture of zinc with alkali solution or of iron with acetic acid can be used. The use of sodium or of another alkali metal in an alcohol such as ethanol, isopropanol, butanol, amyl or isoamyl alcohol or phenol is also suitable. An aluminium-nickel alloy in alkaline aqueous solution, if desired with addition of ethanol, can further be used. Sodium amalgam or aluminium amalgam in aqueous-alcoholic or aqueous solution is also suitable for generation of the nascent hydrogen. The reaction can also be carried out in the heterogeneous phase, an aqueous and a benzene or toluene phase expediently being used.

Complex metal hydrides, such as $LiAlH_4$, $NaBH_4$, diisobutylaluminium hydride or $NaAl(OCH_2CH_2OCH_3)_2H_2$ and also diborane can further be employed particularly advantageously as reducing agents, if desired with addition of catalysts such as $BF_3$, $AlCl_3$ or LiBr. Suitable solvents for this are in particular ethers, such as diethyl ether, di-n-butyl ether, THF, dioxane, diglyme or 1,2-dimethoxyethane and also hydrocarbons such as benzene. For reduction with $NaBH_4$, alcohols such as methanol or ethanol, and further water and aqueous alcohols are primarily suitable as solvents. According to these methods, the reduction is preferably carried out at temperatures between −80° and +150°, in particular between about 0° and about 100°.

The —CO— groups in the acid amides can particularly advantageously be reduced to $CH_2$ groups using $LiAlH_4$ in THF at temperatures between about 0° and 66°.

It is moreover possible to carry out certain reductions by means of $H_2$ gas under the catalytic action of transition metals, such as e.g. Raney Ni or Pd. In this manner, e.g. Cl, Br, I, SH or in certain cases also OH groups can be replaced by hydrogen. Nitro groups can also be converted to $NH_2$ groups by catalytic hydrogenation using $Pd/H_2$ in methanol.

A compound of the formula I can furthermore be converted into another compound of the formula I by methods known per se.

Ethers of the formula I in which, for example, $R^3$, $R^4$ and/or $R^5$ are an OA group can be cleaved in a manner known per se, the corresponding hydroxy derivatives being formed. E.g. the ethers can be cleaved by treating with dimethyl sulfide-boron tribromide complex, e.g. in toluene, ethers such as THF or dimethyl sulfoxide, or by fusing with pyridine or aniline hydrohalides, preferably pyridine hydrochloride, at about 150°– 250°.

The phenyl rings of the compounds of the formula I can be chlorinated, brominated or alkylated, if side reactions are to be excluded, under the conditions of the Friedel-Crafts Reactions by reacting the corresponding halogen or alkyl chloride or alkyl bromide respectively with the compound of the formula I to be derivatized under Lewis acid catalysis, such as e.g. $AlCl_3$, $FeBr_3$ or Fe, at temperatures between 30° and 150°, expediently between 50° and 150°, in an inert solvent, such as e.g. hydrocarbons, THF or carbon tetrachloride.

It is further possible to convert a compound of the formula I in which X=NH to corresponding compounds of the formula I in which X=NA or NAc by alkylation or acylation, according to methods such as are generally customary and known for amines.

The compounds of the formula I can have one or two asymmetric centres. They can therefore be obtained during their preparation as racemates or, if optically active starting substances are used, also in optically active form. If the compounds have two asymmetric centres, then they are in general obtained during the synthesis as mixtures of racemates, from which the individual racemates can be isolated in pure form, for example by recrystallizing from inert solvents. If desired, the racemates obtained can be mechanically or chemically resolved into their optical antipodes by methods known per se. Preferably, diastereomers are formed from the racemate by reaction with an optically active resolving agent.

Suitable resolving agents are e.g. optically active acids, such as the D- and L- forms of tartaric acids dibenzoyltartaric acid, diacetyltartaric acid, camphorsulfonic acids, mandelic acid, malic acid, or lactic acid. The various forms of the diastereomers can be separated in a manner known per se, e.g. by a fractional crystallization, and the optically active compounds of the formula I can be liberated from the diastereomers in a manner known per se.

A base of the formula I obtained can be converted into the respective acid addition salt using an acid. Acids suitable for this reaction are those which yield physiologically acceptable salts. Inorganic acids can thus be used, e.g. sulfuric acid, hydrohalic acids such as hydrochloric acid or hydrobromic acid, phosphoric acids such as orthophosphoric acid, nitric acid, sulfamic acid, and further organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, malic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid.

The free bases of the formula I can, if desired, be liberated from their salts by treatment with strong bases such as sodium hydroxide or potassium hydroxide, sodium carbonate or potassium carbonate, if no further acidic groups are present in the molecule. In those cases where the compounds of the formula I have free acidic groups, salt formation can likewise be achieved by treatment with bases. Suitable bases are alkali metal hydroxides, alkaline earth metal hydroxides or organic bases in the form of primary, secondary or tertiary amines.

The invention further relates to the use of the compounds of the formula I and their physiologically acceptable salts for the production of pharmaceutical preparations, in particular by non-chemical routes. In this process, they can be brought into a suitable dosage form together with at least one excipient or auxiliary and if desired in combination with one or more other active compounds.

The invention further relates to compositions, in particular pharmaceutical preparations, containing at least one compound of the formula I and/or one of its physiologically acceptable salts. These preparations can be employed as medicaments in human and veterinary medicine. Suitable excipients are organic or inorganic substances which are suitable for enteral (e.g. oral) or parenteral administration or topical application and do not react with the novel compounds, for example water, vegetable oils, benzyl alcohols, polyethylene glycols, gelatine, carbohydrates such as lactose or starch, magnesium stearate, talc, petroleum jelly. Tablets, sugar-coated tablets, capsules, syrups, juices, drops or suppositories are used in particular for enteral administration, solutions, preferably oily or aqueous solutions, and further suspensions, emulsions or implants are used for parenteral administration and ointments, creams or powders are used for topical application. The novel compounds can also be lyophilized and the lyophilisates obtained used e.g. for the production of injection preparations.

The preparations indicated can be sterilized and/or contain auxiliaries such as lubricants, preservatives, stabilizers and/or wetting agents, emulsifiers, salts for affecting the osmotic pressure, buffer substances, colorants, flavorings and/or aromatizers. If desired, they can also contain one or more other active compounds, e.g. one or more vitamins.

The compounds of the formula I and their physiologically acceptable salts can be used in the therapeutic treatment of the human or animal body and in the control of diseases. They are suitable in particular for the treatment of arrhythmias and of tachycardias.

The substances according to the invention are as a rule administered here in analogy to known antiarryhthmic substances such as aprindine, flecainide or amiodarone, preferably in doses between about 1 and 100 mg, in particular between 2 and 20 mg, per dosage unit.

The daily dose is preferably between about 0.02 and 2 mg/kg of body weight. The specific dose for each intended patient depends, however, on all sorts of factors, for example on the activity of the specific compound employed, on the age, body weight, general state of health, sex, on the diet, on the time and route of administration, and on the excretion rate, pharmaceutical combination and severity of the particular disease to which the therapy applies. Oral administration is preferred.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. p 43213366.9, filed Jun. 26, 1993, is hereby incorporated by reference.

In the following examples, "customary working up" means:

If necessary, water or dilute sodium hydroxide solution is added, the mixture is extracted with an organic solvent such as ethyl acetate, chloroform or dichloromethane, the organic phase is separated off, dried over sodium sulfate, filtered and evaporated, and the residue is purified by chromatography on silica gel and/or crystallization.

EXAMPLE 1

5.4 g of 2-(6,7,8,9-tetrahydro-5H-benzocyclohepten-5-yl)ethyl bromide [obtainable by reaction of 6,7,8,9-tetrahydro-5H-benzocyclohepten-5-one with diethylethoxycarbonyl methanephosphonate, subsequent hydrogenation with $H_2$/Pd-C, reduction with $BH_3 \times THF$ to the alcohol and subsequent substitution to give the bromide] 6.7 g of 4-(3,4-dimethoxyphenyl)piperidine hydrochloride, 5.8 g of $K_2CO_3$ and 3.6 g of KI are dissolved in 160 ml of ethyl methyl ketone and the mixture is boiled for 3 hours. Customary working up gives 1-(2-( 6,7,8,9-tetrahydro-5H-benzocyclohepten-5-yl)ethyl)-4-( 3,4-dimethoxyphenyl)piperidine.

Subsequent reaction with fumaric acid yields, after crystallization, the corresponding fumarate, m.p. 127°–128°.

The following are obtained analogously by reaction of 4-(3,4-dimethoxyphenyl)piperidine hydrochloride
with 2-(2,3,4,5-tetrahydro-1-benzoxepin-5-yl)ethyl bromide: 1-(2-(2,3,4,5-tetrahydro-1-benzoxepin-5-yl)ethyl)-4-(3,4-dimethoxyphenyl)piperidine, fumarate, m.p. 163°;
with 2-(2,3,4,5-tetrahydro-6-amino-1-benzoxepin- 5-yl) ethyl bromide: 1-(2-(2,3,4,5-tetrahydro-6-amino- 1-benzoxepin-5-yl)ethyl)-4-(3,4-dimethoxyphenyl)piperidine;
with 2-(2,3,4,5-tetrahydro-6-acetylamino-1-benzoxepin-5-yl)ethyl bromide: 1-(2-(2,3,4,5-tetrahydro-6-acetylamino- 1-benzoxepin-5-yl)ethyl)-4-(3,4-dimethoxyphenyl)piperidine;
with 2-(2,3,4,5-tetrahydro-6-methoxy-1-benzoxepin- 5-yl) ethyl bromide: 1-(2-(2,3,4,5-tetrahydro-6-methoxy-1-benzoxepin-5-yl)ethyl)-4-(3,4-dimethoxyphenyl)piperidine;
with 2-(2,3,4,5-tetrahydro-7-chloro-1-benzoxepin- 5-yl) ethyl bromide: 1-(2-(2,3,4,5-tetrahydro-7-chloro- 1-benzoxepin-5-yl)ethyl)-4-(3,4-dimethoxyphenyl)piperidine;
with 2-(2,3,4,5-tetrahydro-6-bromo-1-benzoxepin- 5-yl) ethyl bromide: 1-(2-(2,3,4,5-tetrahydro-6-bromo- 1-benzoxepin-5-yl)ethyl)-4-(3,4-dimethoxyphenyl)piperidine;
with 2-(2,3,4,5-tetrahydro-6-chloro-1-benzoxepin-5-yl) ethyl bromide: 1-(2-(2,3,4,5-tetrahydro-6-chloro- 1-benzoxepin-5-yl)ethyl)-4-(3,4-dimethoxyphenyl)piperidine;
with 2-(2,3,4,5-tetrahydro-7-hydroxy, 1-benzoxepin-5-yl) ethyl bromide: 1-(2-(2,3,4,5-tetrahydro-7-hydroxy-1-benzoxepin-5-yl)ethyl)-4-(3,4-dimethoxyphenyl)piperidine;
with 2-(2,3,4,5-tetrahydro-7-amino-1-benzoxepin-5-yl) ethyl bromide: 1-(2-(2,3,4,5-tetrahydro-7-amino- 1-benzoxepin-5-yl)ethyl)-4-(3,4-dimethoxyphenyl)piperidine;
with 2-(2,3,4,5-tetrahydro-6-acetoxy-1-benzoxepin-5-yl) ethyl bromide: 1-(2-(2,3,4,5-tetrahydro-6-acetoxy- 1-benzoxepin-5-yl)ethyl)-4-(3,4-dimethoxyphenyl)piperidine;
with 2-(2,3,4,5-tetrahydro-7-methoxy-1-benzoxepin-5-yl) ethyl bromide: 1-(2-(2,3,4,5-tetrahydro-7-methoxy-1-benzoxepin-5-yl)ethyl)-4-(3,4-dimethoxyphenyl)piperidine.

EXAMPLE 2

A suspension of 0.6 g of lithium aluminium hydride in 35 ml of THF is treated dropwise with stirring under inert reaction conditions with a solution of 6.3 g of 1-(indan-1-ylacetyl)-4-(3,4-dimethoxyphenyl)piperidine [obtainable by reaction of 1-indanone with diethylethoxycarbonyl methanephosphonate, subsequent hydrogenation with $H_2$/Pd-C, conversion of the ester present to an acid chloride and amide formation with 4-(3,4-dimethoxyphenyl)piperidine] in 70 ml of THF and the mixture is boiled for 2 hours. A further 0.8 g of lithium aluminium hydride is then added and the mixture is refluxed for a further 3 hours. The reaction mixture is then treated with methanol and subsequently with water and worked up in the customary manner. Chromatography (methyl tertbutyl ether/petroleum ether/diethylamine) gives 1-(2-(indan- 1-yl)ethyl)-4-(3,4-dimethoxyphenyl)piperidine.

Subsequent reaction with fumaric acid yields, after crystallization, the corresponding fumarate, m.p. 156°–157°.

The following are obtained analogously by reduction with lithium aluminium hydride and subsequent salt formation
from 1-(tetralin-1-ylacetyl)-4-(3,4-dimethoxyphenyl)piperidine: 1-(2-(tetralin-1-yl)ethyl)-4-(3,4-dimethoxyphenyl)piperidine, fumarate, m.p. 154°–156°;
from 6-[4-(tetralin-1-ylacetyl)-piperazino]-1,4-benzodioxane: 6-[4-(2-(tetralin-1-yl)ethyl)piperazino]- 1,4-benzodioxane, fumarate, m.p. 160°–161°;
from 1-(2,3-dihydrobenzofuran-3-ylacetyl)-4-(3,4-dimethoxyphenyl)piperidine: 1-(2-(2,3-dihydrobenzofuran- 3-yl)ethyl)-4-(3,4-dimethoxyphenyl)piperidine, fumarate, m.p. 149°–150°.

The following are obtained analogously by reduction with lithium aluminium hydride
from 1-(6-methoxy-tetralin-1-ylacetyl)-4-(3,4-dimethoxyphenyl)piperidine: 1-(2-(6-methoxytetralin-1-yl) ethyl)-4-(3,4-dimethoxyphenyl)piperidine;
from 6-[4-(6-amino-tetralin-1-ylacetyl)piperazino]-1,4-benzodioxane: 6-[4-(2-(6-aminotetralin-1-yl)ethyl)piperazino]-1,4-benzodioxane;
from 1-(1,2,3,4-tetrahydro-6-chloroquinolin-4-yl-acetyl)-4-(3,4-dimethoxyphenyl)piperidine; 1-(2-(1,2,3,4-tetrahydro-6-chloroquinolin-4-yl)ethyl)- 4-(3,4-dimethoxyphenyl)piperidine;
from 1-(2,3-dihydro-5-methoxybenzofuran-3-ylacetyl)-4-(3,4-dimethoxyphenyl)piperidine: 1-(2-(2,3-dihydro-5-methoxybenzofuran-3-yl)ethyl)-4-( 3,4-dimethoxyphenyl)piperidine;
from 1-(tetralin-1-ylacetyl)-4-(3,4-dichlorophenyl)piperidine: 1-(2-(tetralin-1-yl)ethyl)-4-(3,4-dichlorophenyl)piperidine;
from 6-[4-(6-bromo-tetralin-1-ylacetyl)piperazino]-1,4-benzodioxane: 6-[4-(2-(6-bromotetralin-1-yl)ethyl)piperazino]-1,4benzodioxane;
from 1-(1,2,3,4-tetrahydro-7-methoxyquinolin-4-ylacetyl)-4-(3,4-dimethoxyphenyl)piperidine; 1-(2-(1,2,3,4-tetrahydro-7-methoxyquinolin-4-yl)ethyl)- 4-(3,4-dimethoxyphenyl)piperidine;

from 1-(2,3-dihydrobenzofuran-3-ylacetyl)-4-(3,4-dichlorophenyl)piperidine: 1-(2-(2,3-dihydrobenzofuran-3-yl)ethyl)-4-(3,4-dichlorophenyl)piperidine.

EXAMPLE 3

A solution of 2.5 g of 1-(2-(1,2,3,4-tetrahydroquinolin-4-yl)ethyl)-4-(3,4-dimethoxyphenyl)piperidine (dihydrochloride, m.p 235°–236°) in 35 ml of THF is treated with a solution of 0.9 g of a acetyl chloride in ml of THF, stirred for 2 hours at-50°, evaporated and worked up in the customary manner. 1-(2-(1,2,3,4-Tetrahydro- 1-acetylquinolin-4-yl) ethyl)-4-(3,4-dimethoxyphenyl)piperidine is obtained.

The compounds below are obtained analogously by acetylation or alkylation of the corresponding tetrahydroquinoline derivatives:

1-(2-(1,2,3,4-tetrahydro-1-methylquinolin-4-yl)ethyl)-4-(3,4-dimethoxyphenyl)piperidine;
1-(2-(1,2,3,4-tetrahydro-1-isopropylquinolin-4-yl)ethyl)-4-(3,4-dimethoxyphenyl)piperidine;
1-(2-(1,2,3,4-tetrahydro-1-propionylquinolin-4-yl)ethyl)-4-(3,4-dimethoxyphenyl)piperidine;
1-(2-(1,2,3,4-tetrahydro-1-ethylquinolin-4-yl)ethyl)-4-( 3,4-dimethoxyphenyl)piperidine;
1-(2-(1,2,3,4-tetrahydro-1-methylquinolin-4-yl)ethyl)-4-(3,4-dichlorophenyl)piperidine;
1-(2-(1,2,3,4-tetrahydro-1-isopropylquinolin-4-yl)ethyl)-4-(3,4-methylenedioxyphenyl)piperidine;
1-(2-(1,2,3,4-tetrahydro-1-propionylquinolin-4-yl)ethyl)-4-(3,4-methylenedioxyphenyl)piperidine;
1-(2-(1,2,3,4-tetrahydro-1-acetylquinolin-4-yl)ethyl)-4-(3,4-methylenedioxyphenyl)piperidine;
1-(2-(1,2,3,4-tetrahydro-1-acetylquinolin-4-yl)ethyl)-4-(4-methoxyphenyl)piperidine;
1-(2-(1,2,3,4-tetrahydro-1-isopropylquinolin-4-yl)ethyl)-4-(4-chlorophenyl)piperidine;
1-(2-(1,2,3,4-tetrahydro-1-propionylquinolin-4-yl)ethyl)-4-(4-methoxyphenyl)piperidine;
1-(2-(1,2,3,4-tetrahydro-1-propylquinolin-4-yl)ethyl)-4-(4-nitrophenyl)piperidine;
1-(2-(1,2,3,4-tetrahydro-1-propionylquinolin-4-yl)ethyl)-4-(4-chlorophenyl)piperidine;
1-(2-(1,2,3,4-tetrahydro-1-isopropylquinolin-4-yl)ethyl)-4-phenyl piperidine;
1-(2-(1,2,3,4-tetrahydro-1-propionylquinolin-4-yl)ethyl)-4-phenyl piperidine;
1-(2-(1,2,3,4-tetrahydro-1-ethylquinolin-4-yl)ethyl)-4-(4-methoxyphenyl)piperidine.

EXAMPLE 4

A mixture of 4.1 g of 1-(2-(tetralin-1-yl)ethyl)- 4-(3,4-dimethoxyphenyl)piperidine (fumarate, m.p. 154°– 156°) 3.2 g of pyridine hydrochloride and 80 ml of pyridine is boiled for 3 hours. It is cooled, evaporated and worked up in the customary manner and gives 1-(2-(tetralin- 1-yl)ethyl)-4-(3,4-dihydroxyphenyl)piperidine.

EXAMPLE 5

3.6 g of 2-(2,3,4,5-tetrahydro-7-cyano-1-benzoxepin-5-yl)ethyl bromide [obtainable starting from 2,3,4,5-tetrahydro-7-cyano-1-benzoexpin-5-one [sic] by reaction with triphenylethylphosphinium bromide, subsequent bromination of the product in the allyl position and reduction of the isolated double bond with diisobutyl-aluminiumhydride (DIBAH)], 1 equivalent of 4-( 3,4-dimethoxyphenyl)piperidine hydrochloride, 3.8 g of $K_2CO_3$ and 2.1 g of KI are dissolved in 120 ml of ethyl methyl ketone and the mixture is boiled for 3 hours. Customary working up gives 1-(2-(2,3,4,5-tetrahydro-7-cyano- 1-benzoxepin-5-yl)ethyl)-4-(3,4-dimethoxyphenyl)piperidine.

The following are obtained analogously by reaction of 4-(3,4-dimethoxyphenyl)piperidine hydrochloride
with 2-(2,3,4,5-tetrahydro-6-cyano-1-benzoxepin-5-yl)ethyl bromide: 1-(2-(2,3,4,5-tetrahydro-6-cyano-1-benzoxepin-5-yl)ethyl)- 4-(3,4-dimethoxyphenyl)piperidine;
with 2-(2,3,4,5-tetrahydro-6-nitro-1-benzoxepin-5-yl)ethyl bromide: 1-(2-(2,3,4,5-tetrahydro-6-nitro-1-benzoxepin-5-yl)ethyl- 4-(3,4-dimethoxyphenyl)piperidine;
with 2-(2,3,4,5-tetrahydro-7-cyano-1-benzoxepin-5-yl)ethyl bromide: 1-(2-(2,3,4,5-tetrahydro-7-cyano-1-benzoxepin-5-yl)ethyl)- 4-(3,4-dimethoxyphenyl)piperidine;
with 2-(2,3,4,5-tetrahydro-8-cyano-1-benzoxepin-5-yl)ethyl bromide: 1-(2-(2,3,4,5-tetrahydro-8-cyano-1-benzoxepin-5-yl)ethyl)- 4-(3,4-dimethoxyphenyl)piperidine;
with 2-(2,3,4,5-tetrahydro-8-nitro-1-benzoxepin-5-yl)ethyl bromide: 1-(2-(2,3,4,5-tetrahydro-8-nitro-1-benzoxepin-5-yl)ethyl)- 4-(3,4-dimethoxyphenyl)piperidine;

EXAMPLE 6

Analogously to Example 5, reaction of 4-(3,4-dimethoxyphenyl)piperidine hydrochloride with 2-(6-nitrotetralin-1-yl)ethyl bromide gives 1-(2-(6-nitrotetralin- 1-yl)ethyl)-4-(3,4-dimethoxyphenyl)piperidine.

EXAMPLE 7

A suspension of 3.2 g of 1-(2-(6-nitrotetralin-1-yl)ethyl)-4-(3,4-dimethoxyphenyl)piperidine in 50 ml of methanol is hydrogenated in the presence of 1.6 g of Pd/C (5%) until the absorption of hydrogen has come to a standstill. The catalyst is filtered off, and the filtrate is worked up in the customary manner and gives 1-(2-(6-aminotetralin-1-yl) ethyl)-4-(3,4-dimethoxyphenyl)piperidine.

EXAMPLE 8

Analogously to Example 2, reduction of 1-(1,2,3,4-tetrahydroquinolin-4-yl-acetyl)-4-(3,4-dimethoxyphenyl)piperidine [obtainable by reaction of 1,2,3,4-tetrahydroquinolin-4-one with diethylethoxycarbonyl methanephosphonate, subsequent hydrogenation with $H_2$/Pd-C, hydrolysis of the ester present and subsequent amide formation with 4-(3,4-dimethoxyphenyl)piperidine] using lithium aluminium hydride gives 1-(2-( 1,2,3,4-tetrahydroquinolin-4-yl)ethyl)-4-(3,4-dimethoxyphenyl)piperidine, m.p. 235°–236° (dihydrochloride).

The examples below relate to pharmaceutical preparations.

Example A

Injection Vials

A solution of 100 g of an active compound of the formula I and 5 g of disodium hydrogen phosphate in 3 l of-double-distilled water is adjusted to pH 6.5 using 2N hydrochloric acid, sterile-filtered, filled into injection vials, lyophilized under sterile conditions and sterile-sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4 \times 2\ H_2O$, 28.48 g of $Na_2HPO_4 \times 12\ H_2O$ and 0.1 g of benzalkonium chloride in 940 ml of double-distilled water. The mixture is adjusted to pH 6.8, made up to 1 l and sterilized by irradiation. This solution can be used in the form of eyedrops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed to give tablets in the customary manner such that each tablet contains 10 mg of active compound.

Example F

Sugar-coated Tablets

Tablets are pressed analogously to Example E and are then coated with a coating of sucrose, potato starch, talc, tragacanth and colorant in the customary manner.

Example G

Capsules 2 kg of active compound of the formula I are filled into hard gelatine capsules in the customary manner such that each capsule contains 20 mg of the active compound.

Example H

Ampoules

A solution of 1 kg of active compound of the formula I in 60 l of double-distilled water is sterile-filtered, filled into ampoules, lyophilized under sterile conditions and sterile-sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A piperidine or piperazine compound of formula I

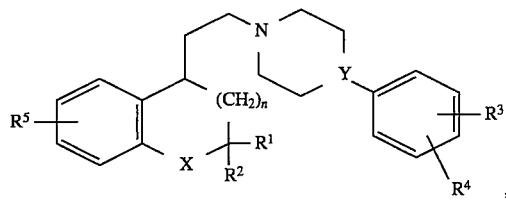

wherein
$R^1$ and $R^2$ are H or A,
$R^3$, $R^4$ and $R^5$ are each independently H, Hal, OH, OA, OAc, $NO_2$, $NH_2$, NHAc, $NHSO_2A$ or CN, or
$R^3$ and $R^4$ together are —O—$(CH_2)_m$—O—,
n is 0, 1 or 2
X is O or $CH_2$, if n=0 or 2, or $CH_2$, NH, NA or NAc, if n=1,
Y is CH or N,
m is 1 or 2,
Hal is F, Cl, Br or I,
A is $C_{1-6}$-alkyl, and
Ac is $C_{1-8}$-alkanoyl $C_{1-10}$-aralkanoyl or $C_{7-11}$-aroyl,
or an enantiomer or a physiologically acceptable salt thereof.

2. A compound according to claim 1, wherein A is $C_{1-3}$-alkyl, OA is methoxy, —NA— is —N-methyl and —$NHSO_2A$ is —$NHSO_2$-methyl.

3. A compound according to claim 1, wherein Ac is $C_{1-8}$-alkanoyl or $C_{7-15}$-aroyl optionally substituted by 1–3 of $C_{1-3}$-alkyl, $C_{1-3}$-alkoxy, $C_{1-3}$-alkylthio, $C_{1-3}$-alkylsulfonyl, $C_{1-3}$-alkylsulfinyl, methylenendioxy, OH, F, Cl, Br, I, $NO_2$, $NH_2$, $C_{1-3}$-alkylamino or di-$C_{1-3}$-alkylamino.

4. A compound according to claim 1, wherein Ac is $C_{1-5}$-alkanoyl.

5. A compound according to claim 1, wherein $R^1$ and $R^2$ are each independently H or methyl.

6. A compound according to claim 1, wherein $R^3$, $R^4$ and $R^5$ are each independently H or methoxy.

7. A compound according to claim 1, wherein $R^5$ is CN.

8. A compound according to claim 1, wherein $R^3$ and $R^4$ together are methylenedioxy or ethylenedioxy.

9. A compound according to claim 1, wherein Y is CH.

10. A compound according to claim 1, wherein
Ia, $R^1$, $R^2$ and $R^5$ are hydrogen and $R^3$ and $R^4$ are methoxy;
Ib, $R^1$, $R^2$ and $R^5$ are hydrogen and $R^3$ and $R^4$ are methylene- or ethylenedioxy;
Ic, $R^1$, $R^2$ and $R^5$ are hydrogen, n is 0, 1 or 2 and X is —$CH_2$—;
Id, $R^1$, $R^2$ and $R^5$ are hydrogen, n is 0, 1 or 2 and X is oxygen;
Ie, $R^1$, $R^2$ and $R^5$ are hydrogen, n=1 and X is NH;
If, $R^1$, $R^2$ and $R^5$ are hydrogen and $R^3$ and $R^4$ are methoxy, X is —$CH_2$— and Y is CH;
Ig, $R^1$, $R^2$ and $R^5$ are hydrogen and $R^3$ and $R^4$ are each methoxy, X is —$CH_2$— and Y is nitrogen;
Ih, $R^1$, $R^2$ and $R^5$ are hydrogen and $R^3$ and $R^4$ are ethylenedioxy, X is —$CH_2$— and Y is nitrogen; or
Ii, $R^1$ and $R^2$ are each methyl, $R^5$ is hydrogen and $R^3$ and $R^4$ are each methoxy.

11. A compound according to claim 1, which is (a) 1-[2-(6,7,8,9-Tetrahydro-5H-benzocyclohepten-5-yl) ethyl] -4-(3,4-dimethoxyphenyl)piperidine;

(b) 5-[2-(4-(3,4-dimethoxyphenyl)-1-piperidinyl)ethyl] -2,3,4,5-tetrahydro-1-benzoxepin;

(c) 3-[2-(4-(3,4-dimethoxyphenyl)-1-piperidinyl)ethyl] -2,3-dihydrobenzofuran;

(d) 1-[2-(tetralin-1-yl)-ethyl]-4-(3,4-dimethoxyphenyl)piperidine;

(e) 1-[2-(indan-1-yl)-ethyl]-4-(3,4-dimethoxyphenyl)piperidine; or (f) 1-[2-(1,2,3,4-tetrahydroquinolin-4-yl)ethyl]-4-(3,4-dimethoxyphenyl)piperidine, or a salt thereof.

12. A pharmaceutical composition, comprising at least one compound of the formula I according to claim 1, or one of it physiologically acceptable salts, and a physiologically acceptable carrier.

13. A method of achieving an antiarrhythmic or positive inotropic effect, comprising administering a compound according to claim 1.

14. A method of treating arrhythmia or tachycardia, comprising administering a compound according to claim 1.

15. A process for the preparation of a piperidine or piperazine derivative of formula I according to claim 1, wherein a compound of formula II

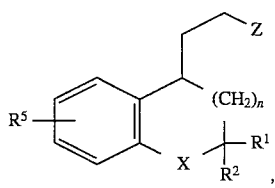

wherein

Z is Cl, Br, OH or a reactive, functionally modified OH group and $R^1$, $R^2$ $R^5$ X and n have the meanings in claim 1, is reacted with a compound of formula III

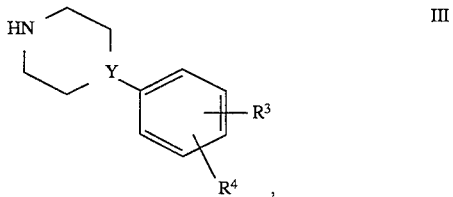

wherein $R^3$, $R^4$ and Y have the meanings in claim 1, or wherein a compound which corresponds to formula I, but at least one $CH_2$ group has a reducible group, is converted into a compound of formula I by reduction, or wherein at least one of $R^3$, $R^4$ $R^5$ or X in a compound of the formula I are converted into other $R^3$, $R^4$, $R^5$ or X or if X=NH, wherein a basic compound of the formula I is converted into one of its physiologically acceptable acid addition salts by treating with an acid.

* * * * *